United States Patent
Fay et al.

(10) Patent No.: US 11,975,218 B2
(45) Date of Patent: May 7, 2024

(54) RADIOTHERAPY PLAN PARAMETERS WITH PRIVACY GUARANTEES

(71) Applicant: Elekta AB (publ), Stockholm (SE)

(72) Inventors: Dominik Fay, Stockholm (SE); Jens Olof Sjolund, Uppsala (SE)

(73) Assignee: Elekta AB (publ), Stockholm (SE)

( * ) Notice: Subject to any disclaimer, the term of this patent is extended or adjusted under 35 U.S.C. 154(b) by 386 days.

(21) Appl. No.: 17/595,488

(22) PCT Filed: Aug. 27, 2019

(86) PCT No.: PCT/EP2019/072792
§ 371 (c)(1),
(2) Date: Nov. 17, 2021

(87) PCT Pub. No.: WO2020/244788
PCT Pub. Date: Dec. 10, 2020

(65) Prior Publication Data
US 2022/0249868 A1 Aug. 11, 2022

Related U.S. Application Data

(60) Provisional application No. 62/857,052, filed on Jun. 4, 2019.

(51) Int. Cl.
*A61N 5/00* (2006.01)
*A61N 5/10* (2006.01)
(Continued)

(52) U.S. Cl.
CPC ......... *A61N 5/1039* (2013.01); *A61N 5/1071* (2013.01); *G06F 21/6245* (2013.01); *G16H 20/40* (2018.01); *G16H 30/40* (2018.01)

(58) Field of Classification Search
None
See application file for complete search history.

(56) References Cited

U.S. PATENT DOCUMENTS

2016/0140300 A1* 5/2016 Purdie ............... G16H 20/40
705/2
2020/0242268 A1* 7/2020 Epasto ............... G06F 16/285
(Continued)

FOREIGN PATENT DOCUMENTS

AU   2019449346   2/2023
CN   114175030    3/2022
(Continued)

OTHER PUBLICATIONS

"Australian Application Serial No. 2019449346, First Examination Report dated Oct. 31, 2022", 3 pgs.
(Continued)

*Primary Examiner* — Hoon K Song
(74) *Attorney, Agent, or Firm* — Schwegman Lundberg & Woessner, P.A.

(57) ABSTRACT

Techniques for producing segmentation with privacy are provided. The techniques include receiving a medical image; processing the medical image with a student machine learning model to estimate radiotherapy plan parameters, the student machine learning model being trained to establish a relationship between a plurality of public training medical images and corresponding radiotherapy plan parameters, the radiotherapy plan parameters of the plurality of public training medical images being generated by aggregating a plurality of radiotherapy plan parameter estimates produced by: processing the plurality of public training medical images with a plurality of teacher machine learning models to generate sets of radiotherapy plan parameter estimates; and reducing respective dimensions of the sets of radiotherapy plan parameter estimates or medical images, the radiotherapy plan parameters of the plurality of public training medical images being perturbed in accordance with (Continued)

privacy criteria; and generating a radiotherapy treatment plan based on the estimated radiotherapy plan parameters.

20 Claims, 8 Drawing Sheets

(51) Int. Cl.
    *G06F 21/62*     (2013.01)
    *G16H 20/40*     (2018.01)
    *G16H 30/40*     (2018.01)

(56) References Cited

U.S. PATENT DOCUMENTS

| | | | |
|---|---|---|---|
| 2021/0146161 A1* | 5/2021 | Sintay | G16H 40/20 |
| 2022/0012637 A1* | 1/2022 | Rezazadegan Tavakoli | G06N 3/088 |

FOREIGN PATENT DOCUMENTS

| | | |
|---|---|---|
| WO | WO-2018048575 A1 | 3/2018 |
| WO | WO-2020244788 A1 | 12/2020 |

OTHER PUBLICATIONS

"Japanese Application Serial No. 2021-571864, Notification of Reasons for Rejection dated Nov. 8, 2022", w English translation, 17 pgs.

"Australian Application Serial No. 2019449346, Response filed Jan. 13, 2023 to First Examination Report dated Oct. 31, 2022", 24 pgs.

Terada, Masayuki, "What is differential privacy", System Control Information, Feb. 2019, vol. 63, No. 2, 58-63.

"International Application Serial No. PCT/EP2019/072792, International Search Report dated Feb. 10, 2020", 4 pgs.

"International Application Serial No. PCT/EP2019/072792, Written Opinion dated Feb. 10, 2020", 7 pgs.

Nicolas, Papernot, et al., "Semi-supervised Knowledge Transfer for Deep Learning from Private Training Data", 5th International Conference on Learning Representations (ICLR 2017), (Apr. 24, 2017), 1-16.

"European Application Serial No. 19761804.4, Response to Communication pursuant to Rules 161 and 162 filed Jul. 18, 2022", 38 pgs.

"Japanese Application Serial No. 2021-571864, Response filed Feb. 3, 2023 to Notification of Reasons for Rejection dated Nov. 8, 2022", w English Claims, 23 pgs.

"Japanese Application Serial No. 2021-571864, Examiners Decision of Final Refusal dated Jun. 6, 2023", w English translation, 11 pgs.

"Japanese Application Serial No. 2021-571864, Appeal of an Adverse Decision—Overseas Applicant filed Oct. 6, 2023", With English Machine Translation, 21 pgs.

"Japanese Application Serial No. 2021-571864, Preliminary Examination Report dated Nov. 28, 2023", w English Translation, 6 pgs.

\* cited by examiner

RADIOTHERAPY PLAN PARAMETERS WITH PRIVACY GUARANTEES

CLAIM FOR PRIORITY

This application is a U.S. National Stage Filing under 35 U.S.C. § 371 from International Application No. PCT/EP2019/072792, filed on Aug. 27, 2019, and published as WO2020/244788 on Dec. 10, 2020, which claims the benefit of priority to U.S. Provisional Application No. 62/857,052, filed Jun. 4, 2019; the benefit of priority of each of which is hereby claimed herein, and which applications and publication are hereby incorporated herein b reference in their entireties.

TECHNICAL FIELD

This disclosure relates generally to radiation therapy or radiotherapy.

BACKGROUND

Radiotherapy is used to treat cancers and other ailments in mammalian (e.g., human and animal) tissue. The direction and shape of the radiation beam should be accurately controlled to ensure the tumor receives the prescribed radiation, and the placement of the beam should be such as to minimize damage to the surrounding healthy tissue (often called the organ(s) at risk (OARs)). Treatment planning can be used to control radiation beam parameters, and a radiotherapy device effectuates a treatment by delivering a spatially varying dose distribution to the patient.

Traditionally, for each patient, a radiation therapy treatment plan ("treatment plan") may be created using an optimization technique based on clinical and dosimetric objectives and constraints (e.g., the maximum, minimum, and mean doses to the tumor and critical organs). The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming trial-and-error process that is complicated by the various OARs, because as the number of OARs increases (e.g., 21 are commonly segmented in a head-and-neck treatment), so does the complexity of the process. OARs distant from a tumor may be easily spared from radiation, while OARs close to or overlapping a target tumor may be difficult to spare.

Segmentation may be performed to identify the OARs and the area to be treated (for example, a planning target volume (PTV)). After segmentation, a dose plan may be created for the patient indicating the desirable amount of radiation to be received by the PTV (e.g., target) and/or the OARs. The PTV may have an irregular volume and may be unique as to its size, shape, and position. A treatment plan can be calculated after optimizing a large number of plan parameters to ensure that enough dose is provided to the PTV while as low a dose as possible is provided to surrounding healthy tissue. Therefore, a radiation therapy treatment plan may be determined by balancing efficient control of the dose to treat the tumor against sparing any OAR. Typically, the quality of a radiation treatment plan may depend upon the level of experience of the planner. Further complications may be caused by anatomical variations between patients.

Machine learning can play a significant role in assisting with creation of radiotherapy treatment plans. Most machine learning models that can be used to create radiotherapy treatment plans are trained on sets of sensitive data (e.g., medical images) that come from other patients and hospitals. Such models fail to protect the privacy of the patients associated with the medical images used in training such machine learning models. Particularly, machine learning models fail to guarantee that it is not possible to infer whether a particular individual was part of the training set.

OVERVIEW

In some embodiments, a computer-implemented method, non-transitory computer-readable medium, and a system comprising a memory and processor are provided for performing privacy based radiotherapy treatment planning by receiving, by processor circuitry, a medical image of a patient; processing, by the processor circuitry, the medical image with a student machine learning model to estimate one or more radiotherapy plan parameters, wherein the student machine learning model is trained to establish a relationship between a plurality of public training medical images and corresponding radiotherapy plan parameters of the public training medical images, wherein the radiotherapy plan parameters of the plurality of public training medical images are generated by aggregating a plurality of radiotherapy plan parameter estimates which have been produced by: processing the plurality of public training medical images with a plurality of teacher machine learning models to generate sets of radiotherapy plan parameter estimates; and reducing respective dimensions of the sets of radiotherapy plan parameter estimates or the plurality of public training medical images, wherein the radiotherapy plan parameters of the plurality of public training medical images are perturbed in accordance with a privacy criteria; and generating, by the processor circuitry, a radiotherapy treatment plan for the patient based on the estimated one or more radiotherapy plan parameters of the medical image of the patient.

In some implementations, the student machine learning model and the plurality of teacher machine learning models are implemented by respective neural networks or deep learning networks.

In some implementations, the computer-implemented method, non-transitory computer-readable medium, and a system comprising a memory and processor perform operations for training the teacher machine learning models based on private medical information comprising private medical images and private radiotherapy plan parameters of the private medical images, wherein the student machine learning model is trained on data that excludes the private medical information.

In some implementations, training the teacher machine learning models comprises: generating disjoint datasets from the private medical information; and training the teacher machine learning models based on respective ones of the disjoint datasets.

In some implementations, the computer-implemented method, non-transitory computer-readable medium, and a system comprising a memory and processor perform operations for generating a first of the plurality of radiotherapy plan parameter estimates by processing the plurality of public training medical images with a first of the plurality of trained teacher machine learning models; generating a second of the plurality of radiotherapy plan parameter estimates by processing the plurality of public training medical images with a second of the plurality of trained teacher machine learning models; reducing a dimension of each of the first and second of the plurality of radiotherapy plan parameter estimates to produce reduced dimension first and second radiotherapy plan parameter estimates; and aggregating the reduced dimension first and second radiotherapy plan parameter estimates.

In some implementations, the first of the plurality of radiotherapy plan parameter estimates includes a first number of entries, and wherein the reduced dimension first radiotherapy plan parameter estimate includes a second number of entries that is smaller than the first number of entries.

In some implementations, aggregating the reduced dimension first and second radiotherapy plan parameter estimates comprises computing a mean, a trimmed mean, a median, or a generalized f-mean of the reduced dimension first and second radiotherapy plan parameter estimates.

In some implementations, aggregating the reduced dimension first and second radiotherapy plan parameter estimates comprises estimating an aggregation of the reduced dimension first and second radiotherapy plan parameter estimates by processing the reduced dimension first and second radiotherapy plan parameter estimates with an aggregation machine learning model, wherein the aggregation machine learning model is trained to establish a relationship between a plurality of training individual radiotherapy plan parameter estimates and aggregated results of the plurality of training individual radiotherapy plan parameter estimates and to minimize an amount of perturbation needed to satisfy the privacy criteria.

In some implementations, the computer-implemented method, non-transitory computer-readable medium, and a system comprising a memory and processor perform operations for perturbing at least one of the reduced dimension first and second radiotherapy plan parameter estimates or the aggregated reduced dimension first and second radiotherapy plan parameter estimates by adding noise based on a selected privacy level to the at least one of the reduced dimension first and second radiotherapy plan parameter estimates or the aggregated reduced dimension first and second radiotherapy plan parameter estimates.

In some implementations, adding noise comprises adding samples from a Gaussian, Beta, Dirichlet, or Laplace distribution to at least one of the reduced dimension first and second radiotherapy plan parameter estimates or the aggregated reduced dimension first and second radiotherapy plan parameter estimates.

In some implementations, the computer-implemented method, non-transitory computer-readable medium, and a system comprising a memory and processor perform operations for increasing a dimension of the perturbed aggregated reduced dimension first and second radiotherapy plan parameter estimates to output the plurality of radiotherapy plan parameters.

In some implementations, increasing the dimension comprises processing the perturbed aggregated reduced dimension first and second radiotherapy plan parameter estimates with a variational autoencoder, autoencoder, principal component analysis, or homomorphic compression.

In some implementations, reducing the dimension of each of the first and second of the plurality of radiotherapy plan parameter estimates comprises processing each of the first and second of the plurality of radiotherapy plan parameter estimates with a variational autoencoder, autoencoder, principal component analysis, or homomorphic compression.

In some implementations, the variational autoencoder, the autoencoder, or the principal component analysis is trained based on a public set of segmentation maps In some implementations, the privacy criteria comprise at least one of differential privacy, Rényi differential privacy, concentrated differential privacy, mutual information, conditional entropy, Fisher information, generative adversarial privacy, or k-anonymity.

In some implementations, the medical image comprises a magnetic resonance (MR) image or computed tomography (CT), and wherein the one or more radiotherapy plan parameters include at least one of labels for the medical image, a three-dimensional volume corresponding to the medical image, a dose distribution, a synthetic CT image, the medical image, a processed version of the medical image, or radiotherapy device parameters.

In some embodiments, a computer-implemented method, non-transitory computer-readable medium, and a system comprising a memory and processor are provided for training a machine learning model to perform privacy based radiotherapy treatment planning by: receiving, by processor circuitry, a public training medical image of a patient; and training, by the processor circuitry, a student machine learning model to estimate one or more radiotherapy plan parameters of the public training medical image by establishing a relationship between a plurality of public training medical images and corresponding radiotherapy plan parameters of the plurality of public training medical images, wherein the radiotherapy plan parameters of the plurality of public training medical images are generated by aggregating a plurality of radiotherapy plan parameter estimates which have been produced by: processing the public training medical images with a plurality of teacher machine learning models to generate sets of radiotherapy plan parameter estimates; and reducing respective dimensions of the sets of radiotherapy plan parameter estimates or the plurality of public training medical images, wherein the radiotherapy plan parameters of the plurality of public training medical images are perturbed in accordance with privacy criteria.

In some implementations, the computer-implemented method, non-transitory computer-readable medium, and a system comprising a memory and processor perform operations for training the teacher machine learning models based on private medical information comprising private medical images and private radiotherapy plan parameters of the private medical images, wherein the student machine learning model is trained on data that excludes the private medical information.

In some implementations, training the teacher machine learning models comprises: generating disjoint datasets from the private medical information; and training the teacher machine learning models based on respective ones of the disjoint datasets.

In some implementations, the computer-implemented method, non-transitory computer-readable medium, and a system comprising a memory and processor perform operations for generating a first of the plurality of radiotherapy plan parameter estimates by processing the plurality of public training medical images with a first of the plurality of trained teacher machine learning models; generating a second of the plurality of radiotherapy plan parameter estimates by processing the plurality of public training medical images with a second of the plurality of trained teacher machine learning models; reducing a dimension of each of the first and second of the plurality of radiotherapy plan parameter estimates to produce reduced dimension first and second radiotherapy plan parameter estimates; and aggregating the reduced dimension first and second radiotherapy plan parameter estimates.

In some implementations, training the student machine learning model comprises, for each of the plurality of public training medical images: obtaining a pair of a given one of the plurality of public training medical images and a given one of the corresponding radiotherapy plan parameters; applying the student machine learning model to the obtained public training medical image to generate an estimate of the radiotherapy plan parameters for the obtained public training medical image; computing a deviation between the estimate of the radiotherapy plan parameters for the obtained public training medical image and the obtained radiotherapy plan parameter; and updating one or more parameters of the student machine learning model based on the computed deviation.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
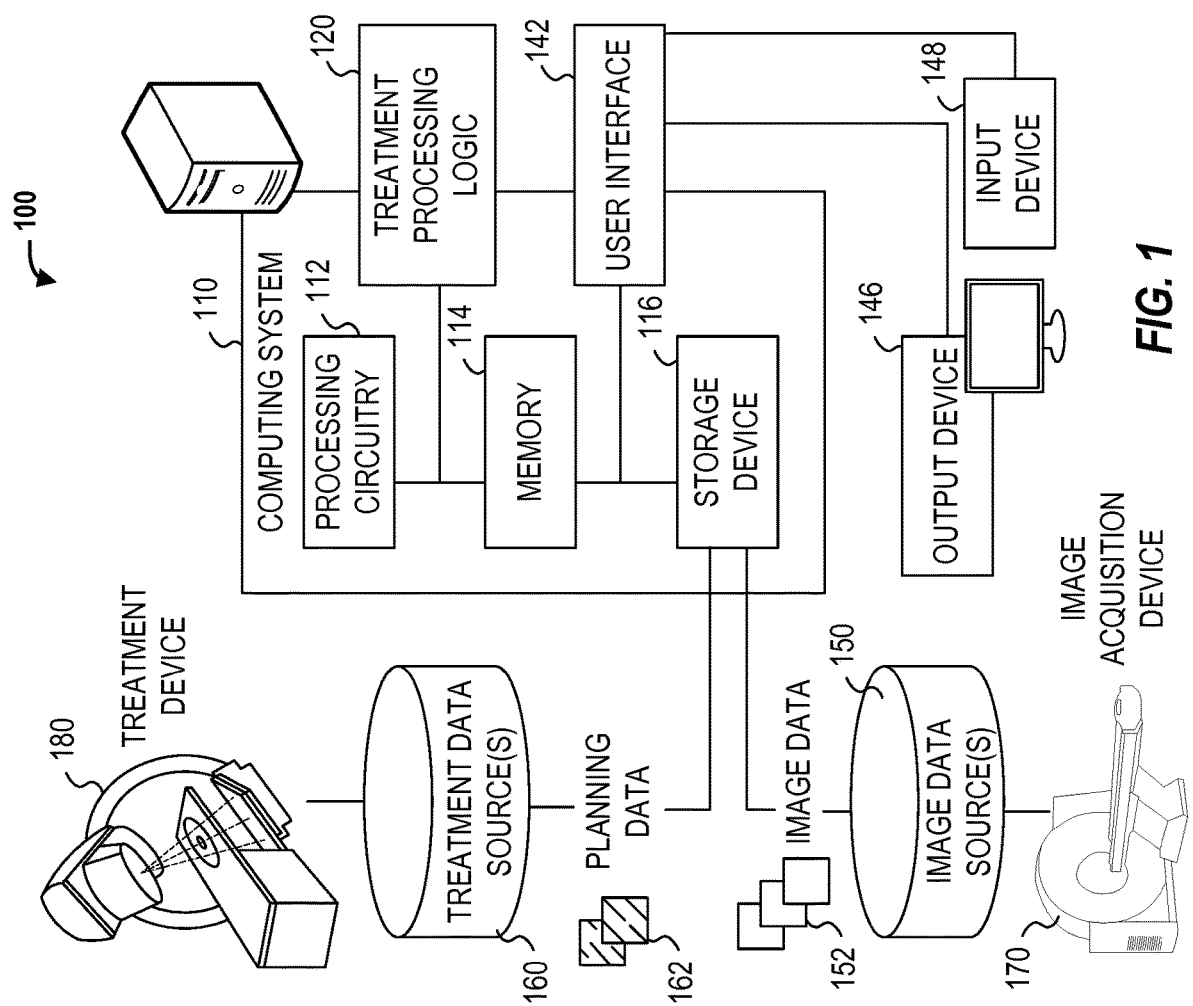
FIG. 1 illustrates an exemplary radiotherapy system adapted for performing treatment plan generation processing, according to some examples.

The present disclosure includes various techniques to generate radiotherapy treatment plans by using a student machine learning (ML) model that has been trained based on public datasets which have been labeled by teacher machine learning models in a way that maintains data privacy (e.g., in a way that satisfies privacy criteria). The technical benefits include reduced computing processing times to generate radiotherapy treatment plans and accompanying improvements in processing, memory, and network resources used to generate radiotherapy treatment plans. The technical benefits also include enhancements in data privacy guarantees for medical image and information, which increases the training data set size used to train ML models and thereby increases accuracy and reliability of ML models used to generate treatment plans. Particularly, because of the enhanced data privacy guarantees, there is an increased likelihood of hospital and patient participation in sharing sensitive medical information for increasing the training data set size. These radiotherapy treatment plans may be applicable to a variety of medical treatment and diagnostic settings or radiotherapy treatment equipment and devices. Accordingly, in addition to these technical benefits, the present techniques may also result in many apparent medical treatment benefits (including improved accuracy of radiotherapy treatment, reduced exposure to unintended radiation, and the like).

Prior approaches discuss ways for providing data privacy for training ML models that predict a single value. Particularly, such prior approaches discuss ways of training teacher ML models on sensitive data and applying such trained teacher models to estimate values for public data. These prior approaches also discuss using the estimated public data to train a student model to be applied to a new data set. Such approaches also consider adding privacy in the process of training the teacher models but do so on very low-dimensional data sets. This makes such approaches unsuitable for radiotherapy applications, such as those involving medical image analysis. This is because radiotherapy applications work with very high dimension data sets (e.g., a computed tomography (CT) volume may have $512^3$ or approximately $10^8$ voxels) which are very highly correlated. Applying the prior art techniques in such scenarios would be computationally prohibitive and inefficient. In addition to the computational resource challenge of applying prior approaches to radiotherapy applications, unreasonable noise levels would be required to provide adequate privacy guarantees because of the high correlation among the high-dimension data sets. For example, if labels of nearby voxels that are highly correlated are treated as a set of independent classification tasks, according to the prior approaches, each medial image voxel would require an unreasonable amount of noise to be added, making it computationally prohibitive, if not impossible, and would need unreasonably large storage resources for the training data to train a useful segmentation ML model.

The disclosed techniques address these challenges by leveraging a dimension adjustment ML model (e.g., a variational autoencoder (VAE)) to encode (reduce) dimensions of the radiotherapy application data which has been labeled by the teacher models before perturbing the data according to privacy criteria. This allows for low noise levels to be introduced in a computationally efficient manner. Subsequently, the dimension adjustment ML model is applied to the perturbed data to decode (increase) the dimension to restore the size of the radiotherapy application data for use in training the student model. Specifically, the disclosed techniques include receiving a medical image and processing the medical image with a student machine learning model to estimate radiotherapy plan parameters. The student machine learning model is trained to establish a relationship between a plurality of public training medical images and corresponding radiotherapy plan parameters. The radiotherapy plan parameters of the plurality of public training medical images are generated by aggregating a plurality of radiotherapy plan parameter estimates produced by: processing the plurality of public training medical images with a plurality of teacher machine learning models to generate sets of radiotherapy plan parameter estimates; and reducing respective dimensions of the sets of radiotherapy plan parameter estimates, the radiotherapy plan parameters of the plurality of public training medical images being perturbed in accordance with privacy criteria. The disclosed techniques generate a radiotherapy treatment plan based on the estimated radiotherapy plan parameters provided by the student model.

According to some embodiments, a VAE is used to compress segmentation maps that are predicted by the teacher models (e.g., teacher ML models that each estimate segmentation labels for CT images, magnetic resonance (MR) images, and PET images) to obtain one low-dimensional feature vector for each teacher model. Specifically, VAEs can learn highly dense non-linear compressions, and the decompressions of VAEs are robust to noisy perturbations of the feature vectors which allows for such an approach to data privacy.

In a specific example, at training time, sensitive (private) data is split into disjoint subsets of data, and a separate teacher segmentation ML model is trained on each subset. After training the teacher ML models on the sensitive data, for each teacher segmentation ML model, the teacher segmentation ML models are applied to unlabeled public datasets. Outputs or predictions on unlabeled public datasets are collected. A VAE is trained on separate, non-sensitive set of segmentation maps, and the teacher segmentation ML predictions on the unlabeled public datasets are compressed using the trained VAE. For each data point, the compressed feature vectors are aggregated across the teacher segmentation ML models using an average and/or a learned function (e.g., an aggregation ML model). The result of the aggregation is perturbed according to a privacy criteria (e.g., using differential privacy techniques) to add noise from a Normal (Gaussian) distribution appropriately scaled to the desired level of privacy. The perturbed predictions are decompressed using the VAE, and a student segmentation ML model is trained on the public dataset which has been labelled by the decompressed predictions. In an embodiment, the student and teacher ML models are implemented using separate implementations of the same ML architecture and processes.

The teacher and student ML models can be trained to estimate any one or more radiotherapy plan parameter. Specifically, in some embodiments, the teacher and student ML models are trained to estimate segmentations as the radiotherapy plan parameter and specifically are trained to segment a radiotherapy medical image, such as a CT image, an MR image, and/or an sCT image. As another example, in some embodiments, the teacher and student ML models are trained to estimate a three-dimensional (3D) model as the radiotherapy plan parameter and specifically are trained to estimate a 3D model of a radiotherapy medical image, such as a CT image, an MR image, and/or an sCT image. As another example, in some embodiments, the teacher and student ML models are trained to estimate a dose distribution as the radiotherapy plan parameter and specifically are trained to estimate a dose distribution based on one or more radiotherapy images. As another example, in some embodiments, the teacher and student ML models are trained to generate or estimate an sCT image as the radiotherapy plan parameter and specifically are trained to estimate an sCT image based on a CT or MR image. As another example, in some embodiments, the teacher and student ML models are trained to estimate radiotherapy device parameters (e.g., control points) as the radiotherapy plan parameter and specifically are trained to estimate control points based on one or more radiotherapy images and/or distance maps specifying (possibly signed) distances to regions of interest.

FIG. 1 illustrates an exemplary radiotherapy system 100 adapted to perform radiotherapy plan processing operations using one or more of the approaches discussed herein. These radiotherapy plan processing operations are performed to enable the radiotherapy system to provide radiation therapy to a patient based on specific aspects of captured medical imaging data and therapy dose calculations or radiotherapy machine configuration parameters. Specifically, the following processing operations may be implemented as part of the treatment processing logic 120. It will be understood, however, that many variations and use cases of the following trained models and treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more private and/or public medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and treatment data source(s) 160. As an example, the radiotherapy processing computing system 110 can be configured to receive a treatment goal of a subject (e.g., from one or more MR images) and generate a radiotherapy treatment plan by executing instructions or data from the treatment processing logic 120, as part of operations to generate treatment plans to be used by the treatment device 180 and/or for output on device 146. In an embodiment, the treatment processing logic includes a student ML model that has been trained on public medical information to estimate one or more radiotherapy parameters. The public information used to train the student ML model is generated by a plurality of teacher ML models that are trained on sensitive or private medical information. The teacher ML models generate the public information (e.g., segmentation or labels for CT images) which is then compressed, aggregated, perturbed according to privacy criteria, and decompressed before being made available to the student ML model for training. In this way, the student ML model can be trained on data (e.g., segmentation or labels of CT images) that satisfies privacy criteria, which enhances and ensures data privacy and does not compromise any individual patient's or hospital's identity.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, training data, software programs (e.g., image processing software, image or anatomical visualization software, artificial intelligence (AI) or ML implementations and algorithms such as provided by deep learning models, ML models, and neural networks (NNs), etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software-based processor (for example, a multi-core design or a plurality of processors each having a multi-core design). The processing circuitry 112 can execute sequences of transitory or non-transitory computer program instructions, stored in memory 114, and accessed from the storage device 116, to perform various operations, processes, and methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, one or more ML model(s) or technique(s) parameters, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, one or more AI model data (e.g., weights and parameters of teacher ML models, student ML models, aggregation ML models, and/or dimension adjustment models), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images) for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data as a result of a treatment plan generated by the treatment processing logic 120. The image data source 150 may also provide or host the imaging data for use in the treatment processing logic 120.

As referred to herein, "public" or "non-sensitive" data includes a collection of data that is publicly available via one or more public databases and which does not contain any data that is subject to data privacy (e.g., the data does not identify a particular individual or identifies an individual who has given express/implied consent). "Private" or "sensitive" data includes a collection of data that includes private hospital and/or patient medical information and is subject to data privacy regulations. In some cases, the private data is not publicly available but is available on a limited access basis to certain organizations and entities without concern for privacy. Such data should ideally not be shared outside of an organization without express permission by a patient or hospital and is maintained in secure, non-publicly accessible databases. In an embodiment, the parameters of the teacher ML models are maintained as private and sensitive data as such parameters can reveal identities of individuals if accessed by an adversary. Data can be received, by way of a query from an external source, and such data can be applied to the private teacher ML models to generate outputs of results. The outputs or results of the teacher ML models can be made publicly accessible as a response to the query, such as by a student ML model, after being subject to privacy criteria according to the disclosed embodiments. The parameters of the student ML model may be publicly accessible.

In an example, computing system 110 may communicate with treatment data source 160 and input device 148 to generate pairs of private prior patient radiotherapy treatment information, such as pairs of labels or segmentations of radiotherapy medical images (e.g., CT, MR and/or sCT images); pairs of a 3D model and one or more corresponding radiotherapy medical images; pairs of a dose distribution and one or more radiotherapy images; pairs of a sCT image and a CT image; pairs of control points and one or more radiotherapy images and/or distance maps; and pairs of individual radiotherapy plan parameter estimates and aggregated results of the plurality of training individual radiotherapy plan parameter estimates. In an example, computing system 110 may communicate with treatment data source 160 and input device 148 to generate pairs of public prior patient radiotherapy treatment information, such as pairs of segmentation maps and compressed dimension segmentation maps; pairs of compressed dimension segmentation maps and uncompressed segmentation maps. Computing system 110 may continue generating such pairs of training data until a threshold number of pairs is obtained.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120. Particularly, treatment processing logic 120 implements a trained student ML model that is applied to a medical image to generate one or more radiotherapy parameters of a treatment plan. In an example, the student ML model segments a radiotherapy medical image, such as a CT image, an MR image, and/or an sCT image. As another example, in some embodiments, the student ML model estimates a 3D model of a radiotherapy medical image, such as a CT image, an MR image, and/or an sCT image. As another example, in some embodiments, the student ML model estimates a dose distribution based on one or more radiotherapy images. As another example, in some embodiments, the student ML model estimates an sCT image based on a CT image. As another example, in some embodiments, the student ML model estimates control points of a radiotherapy treatment device based on one or more radiotherapy images and/or MR scan distance maps.

In addition, the processing circuitry 112 may utilize software programs to generate intermediate data such as updated parameters to be used, for example, by a NN model, machine learning model, treatment processing logic 120, or other aspects involved with generation of a treatment plan as discussed herein. Further, such software programs may utilize the treatment processing logic 120 to produce new or updated treatment plan parameters for deployment to the treatment data source 160 and/or presentation on output device 146, using the techniques further discussed herein. The processing circuitry 112 may subsequently then transmit the new or updated realizable treatment plan parameters via a communication interface and the network to the treatment device 180, where the radiation therapy plan will be used to treat a patient with radiation via the treatment device 180, consistent with results of the trained student ML model implemented by the treatment processing logic 120 (e.g., according to the processes discussed below in connection with FIGS. 3 and 4).

In the examples herein, the processing circuitry 112 may execute software programs that invoke the treatment processing logic 120 to implement functions of ML, deep learning, NNs, and other aspects of artificial intelligence for treatment plan generation from an input radiotherapy medical information (e.g., CT image, MR image, and/or sCT image and/or dose information). For instance, the processing circuitry 112 may execute software programs that train, analyze, predict, evaluate, and generate a treatment plan parameter from received radiotherapy medical information as discussed herein.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 152 may also include or be associated with medical image processing data (for example, training images, and ground truth images, contoured images, and dose images). In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, including control points of a radiotherapy treatment device, such as couch position, beam intensity, beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information (e.g., control points) may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may use to input information to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT or MRI volume. Such 2D slices can be acquired by the image acquisition device 170 in "near real time" while a patient is undergoing radiation therapy treatment (for example, when using the treatment device 180 (with "near real time" meaning acquiring the data in at least milliseconds or less)).

The treatment processing logic 120 in the radiotherapy processing computing system 110 implements a student ML model, which involves the use of a trained (learned) student ML model. This ML model may be provided by a NN trained as part of a NN model. One or more teacher ML models may be provided by a different entity or at an off-site facility relative to treatment processing logic 120 and is accessible by issuing one or more queries to the off-site facility. The teacher ML models may include architectures and processes that complement that of the student ML model. The teacher ML models are each implemented using a same or common set of ML parameters that are private, and the student ML model is implemented using a set of public ML parameters. The discussions pertaining to ML models are equally applicable to any ML model discussed herein.

Machine learning (ML) algorithms or ML models or techniques can be summarized as function approximation. Training data consisting of input-output pairs of some type (e.g., CT-images with segmentations) are acquired from, e.g., expert clinicians, and a function is "trained" to approximate this mapping. Some methods involve NNs. In these, a set of parametrized functions $A_\theta$ are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem such as Equation 1:

$$\min_\theta \sum_{m=1}^{M} \|A_\theta(x_m) - y_m\|^2 \quad (1)$$

Once the network has been trained (e.g., $\theta$ has been selected), the function $A_\theta$ can be applied to any new input. For example, in the above setting of segmentation of CT images, a never before seen CT image can be fed into $A_\theta$, and a segmentation is estimated that matches what an expert clinician would find. In some cases, an autoencoder which is an unsupervised model can be trained by attempting to reconstruct the inputs, such as by setting y=x in Equation 1.

Simple NNs consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier, the number of input layer nodes typically equals the number of features for each of a set of objects being sorted into classes, and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function y=f(x) including non-linear functions. In ML, an assumption is that the training and test data are both generated by the same data-generating process, $p_{data}$, in which each $\{x_i, y_i\}$ sample is identically and independently distributed (i.i.d.). In ML, the goals are to minimize the training error and to make the difference between the training and test errors as small as possible. Underfitting occurs if the training error is too large; overfitting occurs when the train-test error gap is too large. Both types of performance deficiency are related to model capacity: large capacity may fit the training data very well but lead to overfitting, while small capacity may lead to underfitting.

Figure 2:
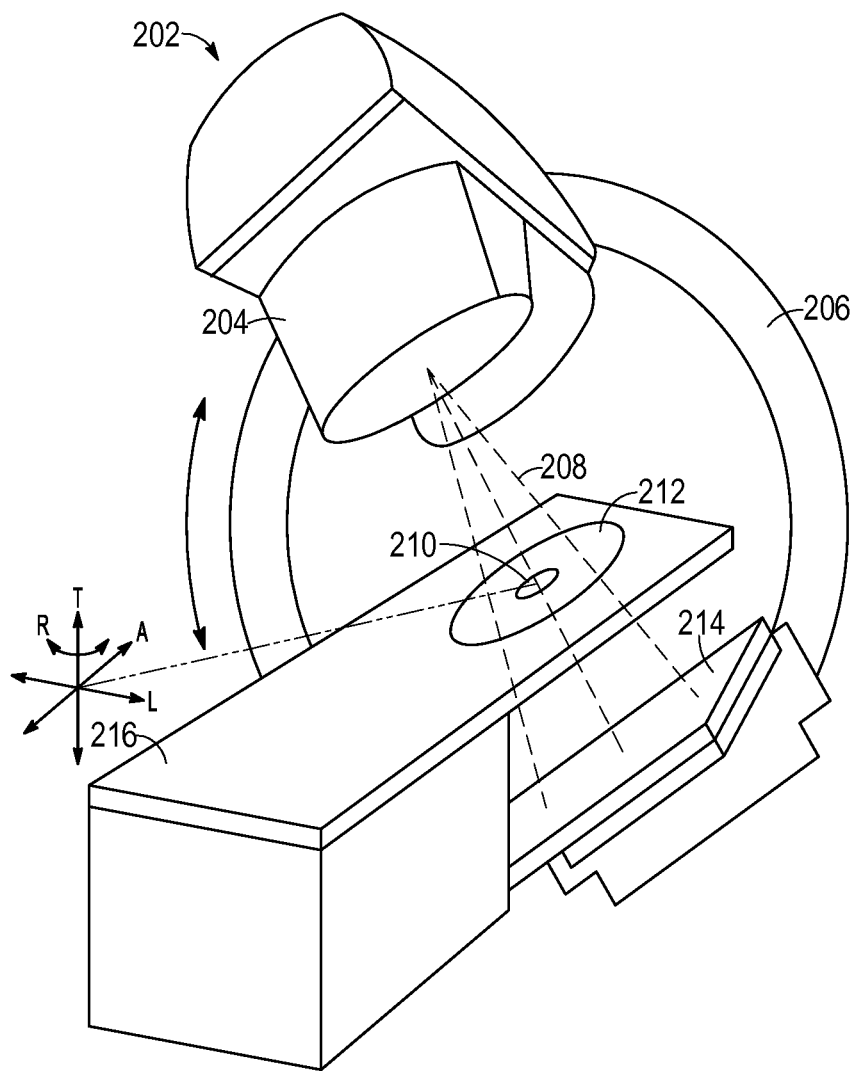
FIG. 2 illustrates an exemplary image-guided radiotherapy device, according to some examples of the disclosure.

FIG. 2 illustrates an exemplary image-guided radiotherapy device 202 that includes a radiation source, such as an X-ray source or a linear accelerator, a couch 216, an imaging detector 214, and a radiation therapy output 204. The radiation therapy device 202 may be configured to emit a radiation therapy beam 208 to provide therapy to a patient. The radiation therapy output 204 can include one or more attenuators or collimators, such as a MLC.

As an example, a patient can be positioned in a region 212, supported by the treatment couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, the gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216's movements or rotations in order to properly position the patient in or out of the radiation therapy beam 208, according to a radiation therapy treatment plan. Both the couch 216 and the gantry 206 are independently moveable from one another in multiple degrees of freedom, which allows the patient to be positioned such that the radiation therapy beam 208 can precisely target the tumor.

The coordinate system (including axes A, T, and L) can have an origin located at an isocenter 210. The isocenter 210 can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204) and, in an example, the imaging detector 214 can be located within a field of the therapy radiation beam 208. The imaging detector 214 can be mounted on the gantry 206, preferably opposite the radiation therapy output 204, so as to maintain alignment with the radiation therapy beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation therapy beam 208, or the imaging detector 214 can be used for imaging the patient's anatomy, such as portal imaging. The control circuitry of radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the therapy radiation beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient consistent with or according to a radiotherapy treatment plan, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, and the like, as would be recognized by one of ordinary skill in the art.

As discussed above, the training data used by treatment processing logic 120 may include a plurality of previous private or public estimated treatment plan parameters paired with prior private or public patient images that are stored in a memory 114. For example, the stored training data may include diagnostic images, treatment images (dose maps), segmentation information, and the like, associated with one or more previous estimated treatment plans. The training data may include a plurality of training samples. Each training sample may comprise a feature vector and a corresponding output vector.

The feature vector may include one or more feature elements. Each feature element may indicate an observation of a medical image (e.g., provided by image acquisition device 140) used in a past radiotherapy session. The observation may be a distance between a volume (e.g., a voxel) and an anatomical region, such as a target or the surface of the body part in the medical image. In another example, the observation may include spatial coordinates of an anatomical region or a probability that an anatomical region includes a particular tissue type. In another example, the feature element may include patient-specific information, responsible physician, organ or volume of interest segmentation data, functional organ modeling data (e.g., serial versus parallel organs, and appropriate dose response models), radiation dosage (e.g., also including DVH information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex), other diseases affecting the patient (e.g., cardiovascular or respiratory disease, diabetes, radiation hypersensitivity syndromes and the like), medications and drug reactions, diet and lifestyle (e.g., smoking or non-smoking), environmental risk factors, tumor characteristics (histological type, tumor grade, hormone and other receptor status, tumor size, vascularity cell type, cancer staging, gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα), and the like. The feature vector may include one or more such feature elements, regardless of whether these feature elements are related to each other or not.

The output vector may include one or more output elements. Each output element may indicate a corresponding estimated plan outcome or parameter in the past radiotherapy session based on the observation(s) included in the feature vector. For example, the output element may include the estimated dose applied or received at a particular spatial location (e.g., a voxel). In another example, the output element may include a patient survival time based on observations such as a treatment type, treatment parameters, patient history, and/or patient anatomy. Additional examples of output elements include, but are not limited to, a normal tissue complication probability (NTCP), a region displacement probability during treatment, or a probability that a set of coordinates in a reference image is mapped to another set of coordinates in a target image. The output vector may include one or more such output elements, regardless of whether these output elements are related to each other or not.

As an example of an embodiment, an output element may include a dose to be applied to a voxel of a particular OAR. Further, a feature element may be used to determine the output element. The feature element may include a distance between the voxel in the OAR and the closest boundary voxel in a target tumor. Therefore, the feature element may include a signed distance x indicating the distance between a voxel in an OAR and the closest boundary voxel in a target for the radiation therapy. The output element may include a dose D in the voxel of the OAR from which x is measured. In some other embodiments, each training sample may correspond to a particular voxel in the target or OAR, such that multiple training samples within the training data correspond to the whole volume of the target or OAR and other anatomical portions subject to the radiotherapy treatment.

Figure 3:
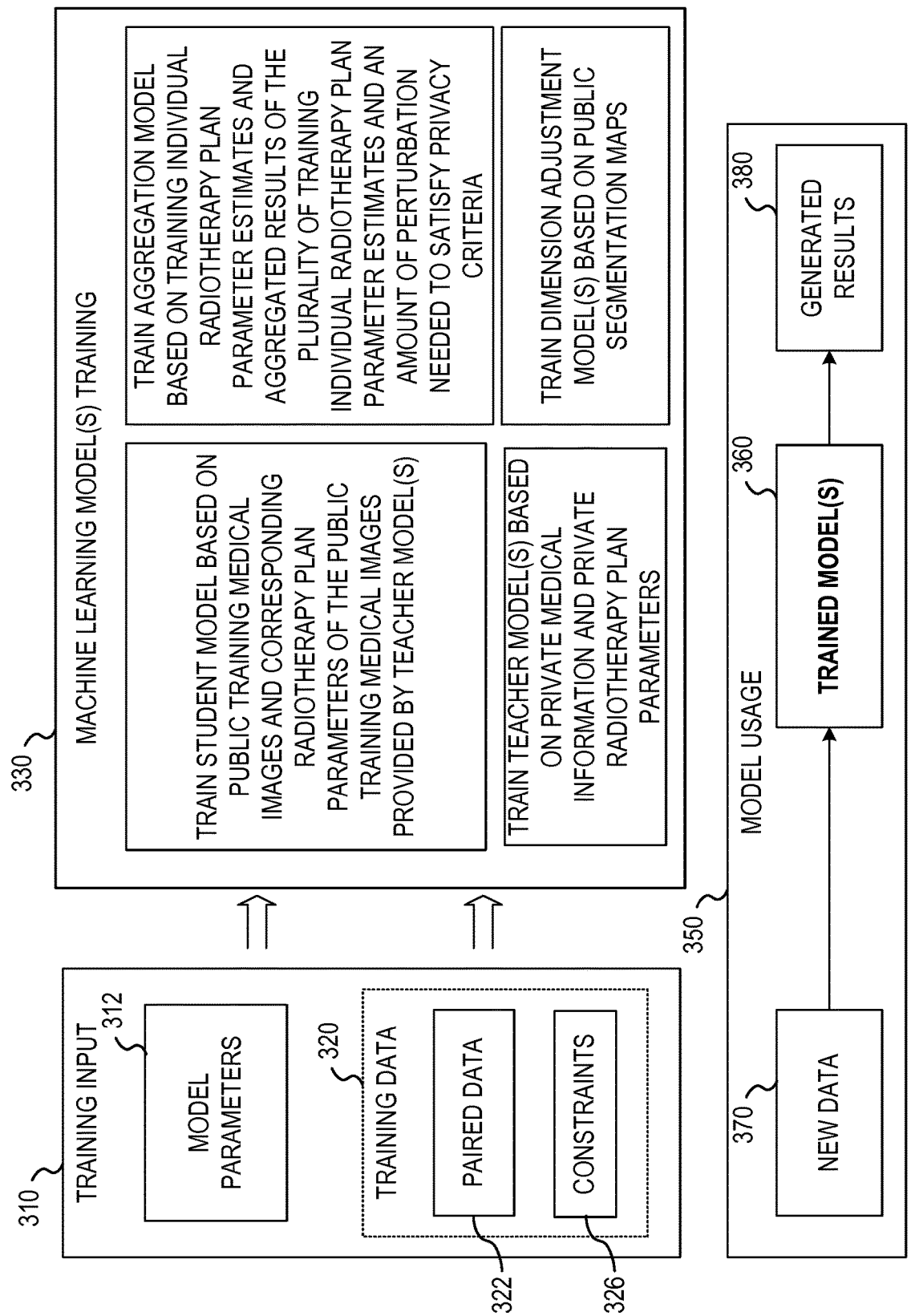
FIG. 3 illustrates an exemplary data flow for training and use of a machine learning model(s), according to some examples of the disclosure.

FIG. 3 illustrates an exemplary data flow for training and use of one or more private and public machine learning models to generate a radiotherapy treatment plan, according to some examples of the disclosure. The data flow includes training input 310, ML model(s) (technique(s)) training 330, and model(s) usage 350.

Training input 310 includes model parameters 312 and training data 320 which may include paired training data sets 322 (e.g., input-output training pairs) and constraints 326. Model parameters 312 stores or provides the parameters or coefficients of corresponding ones of machine learning models $\hat{A}_\theta$. Model parameters 312 may include private parameters for teacher ML models and aggregation models and public parameters for the student model and the dimension adjustment models. The model parameters 312 may be shared and the same for each teacher ML model $\hat{A}_\theta$. The model parameters 312 for the student ML model $\hat{A}_\theta$ may differ from those of the teacher ML model even though the teacher and student ML models have the same architecture and processes. During training, these parameters 312 are adapted based on the input-output training pairs of the training data sets 322. After the parameters 312 are adapted (after training), the parameters are used by trained models 360 to implement the respective one of the trained machine learning models $\hat{A}_\theta$ (e.g., the trained student model $\hat{A}_\theta$, the trained teacher model $\hat{A}_\theta$, the trained aggregation model $\hat{A}_\theta$, and/or the trained dimension adjustment model $\hat{A}_\theta$) on a new set of data 370.

Training data 320 includes constraints 326 which may define the physical constraints of a given radiotherapy device. The training data sets 322 may include sets of private and public input-output pairs, such as a pairs of private prior patient radiotherapy treatment information, such as pairs of labels or segmentations of radiotherapy medical images (e.g., CT, MR and/or sCT images); pairs of a 3D model and one or more corresponding radiotherapy medical images; pairs of a dose distribution and one or more radiotherapy images; pairs of a sCT image and a CT image; pairs of control points and one or more radiotherapy images and/or distance maps; and pairs of individual radiotherapy plan parameter estimates and aggregated results of the plurality of training individual radiotherapy plan parameter estimates; pairs of public prior patient radiotherapy treatment information, such as pairs of segmentation maps and compressed dimension segmentation maps; and pairs of compressed dimension segmentation maps and uncompressed segmentation maps. Some components of training input 310 may be stored at a different off-site facility or facilities than other components. For example, private parameters and private training data pairs may include sensitive or private information and should be restricted for access by only authorized parties or queries.

Machine learning model(s) training 330 trains one or more machine learning techniques $\hat{A}_\theta$ based on the private and public sets of input-output pairs of training data sets 322. For example, the model training 330 may train the student ML model parameters 312 by minimizing a first loss function based on public training patient input data and the corresponding radiotherapy plan parameters that have been generated using the teacher ML models and that satisfy privacy criteria. For example, the treatment model training 330 may train the teacher ML model parameters 312 by minimizing a second loss function based on private training patient input data and the corresponding private radiotherapy plan parameters. For example, the treatment model training 330 may train aggregation ML model parameters 312 by minimizing a third loss function based on individual radiotherapy plan parameter estimates and aggregated results of a plurality of training individual radiotherapy plan parameter estimates and an amount of perturbation needed to satisfy privacy criteria. For example, the treatment model training 330 may train the dimension adjustment ML model parameters 312 (e.g., a VAE encoder and decoder, an autoencoder, and/or principal component analysis) by minimizing a fourth loss function based on public segmentation maps. In some embodiments, the teacher ML model, the aggregation ML model and the dimension adjustment ML model are trained in parallel or sequentially before the student ML model is trained.

The result of minimizing these loss functions for multiple sets of training data trains, adapts, or optimizes the model parameters 312 of the corresponding ML models. Model training 330 may be performed in accordance with the process and dataflow described in connection with FIGS. 4A and 4B. In this way, the student ML model is trained to establish a relationship between the un-labelled public radiotherapy medical information and estimated radiotherapy plan parameters that are provided and privatized by the teacher ML models.

In some embodiments, after each of the machine learning models $\hat{A}_\theta$ is trained, new data 370 including one or more patient input parameters (e.g., an MR image, a medical image, segmentation information of an object of interest associated with the patient, or dose prescription information) may be received. The trained machine learning technique $\hat{A}_\theta$ may be applied to the new data 370 to generate generated results 380 including one or more parameters of a radiotherapy treatment plan. For example, after being trained on sensitive private medical information, the trained teacher ML models 360 may be applied to public radiotherapy information (e.g., public medical images) to generate respective one or more radiotherapy parameters (e.g., labels of a CT image, an sCT image corresponding to a CT image, the medical images, processed versions of the medical images, a dose distribution for an image, and/or control points of a radiotherapy treatment device corresponding to the radiotherapy images and/or MR scan distance maps) of a treatment plan. The generated one or more radiotherapy parameters of the treatment plan are processed by the trained dimension adjustment ML model 360 to reduce a dimension of the one or more radiotherapy parameters of the treatment plan (e.g., by processing the plurality of radiotherapy plan parameters with a variational autoencoder, autoencoder, principal component analysis, or homomorphic compression). Then, the reduced dimension one or more radiotherapy parameters of the treatment plan are processed by the trained aggregation ML model 360 (e.g., which computes a mean, a trimmed mean, a median, or a generalized f-mean of the reduced dimension radiotherapy plan parameters) and are perturbed according to a privacy criteria (e.g., differential privacy, Rényi differential privacy, concentrated differential privacy, mutual information, conditional entropy, Fisher information, generative adversarial privacy, or k-anonymity).

In some embodiments, after each of the machine learning models $\hat{A}_\theta$ is trained, new data 370 including one or more patient input parameters (e.g., an MR image, a medical image, segmentation information of an object of interest associated with the patient, or dose prescription information) may be received. The trained machine learning technique $\hat{A}_\theta$ may be applied to the new data 370 to generate generated results 380 including one or more parameters of a radiotherapy treatment plan. For example, the new data 370 may include public medical images which are processed by the trained dimension adjustment ML model 360 to reduce a dimension of the public medical images in the new data 370 plan (e.g., by processing the medical images with a variational autoencoder, autoencoder, principal component analysis, or homomorphic compression). After being trained on sensitive private medical information, the trained teacher ML models 360 may be applied to reduced dimension public medical images) to generate respective one or more radiotherapy parameters (e.g., labels of a CT image, an sCT image corresponding to a CT image, the medical images, processed versions of the medical images, a dose distribution for an image, and/or control points of a radiotherapy treatment device corresponding to the radiotherapy images and/or MR scan distance maps) of a treatment plan. Then, the generated one or more radiotherapy parameters of the treatment plan are processed by the trained aggregation ML model 360 (e.g., which computes a mean, a trimmed mean, a median, or a generalized f-mean of the reduced dimension radiotherapy plan parameters) and are perturbed according to a privacy criteria (e.g., differential privacy, Rényi differential privacy, concentrated differential privacy, mutual information, conditional entropy, Fisher information, generative adversarial privacy, or k-anonymity) to be used to train the student ML model. Alternatively, the generated one or more radiotherapy parameters of the treatment plan are first perturbed according to a privacy criteria (e.g., differential privacy, Rényi differential privacy, concentrated differential privacy, mutual information, conditional entropy, Fisher information, generative adversarial privacy, or k-anonymity), processed by the trained aggregation ML model 360 (e.g., which computes a mean, a trimmed mean, a median, or a generalized f-mean of the reduced dimension radiotherapy plan parameters) and then the student ML model is then trained based on the output of the aggregation ML model 360.

In an embodiment, the perturbation is performed by adding noise comprising samples from a Gaussian, Beta, Dirichlet, or Laplace distribution. Then, the perturbed aggregated one or more radiotherapy parameters of the treatment plan are processed by the trained dimension adjustment ML model 360 to restore their dimension (increase their dimension) (e.g., by processing the perturbed aggregated plurality of radiotherapy plan parameters with a variational autoencoder, autoencoder, principal component analysis, or homomorphic compression) and are then provided to train the student ML model 360. After the student ML model 360 is trained, the trained student ML model 360 is applied to new radiotherapy information (e.g., a medical image) to generate one or more radiotherapy parameters (e.g., labels of a CT image, an sCT image corresponding to a CT image, a dose distribution for an image, the medical image, a processed version of the medical image, and/or control points of a radiotherapy treatment device corresponding to the radiotherapy images and/or MR scan distance maps).

Figure 4A:
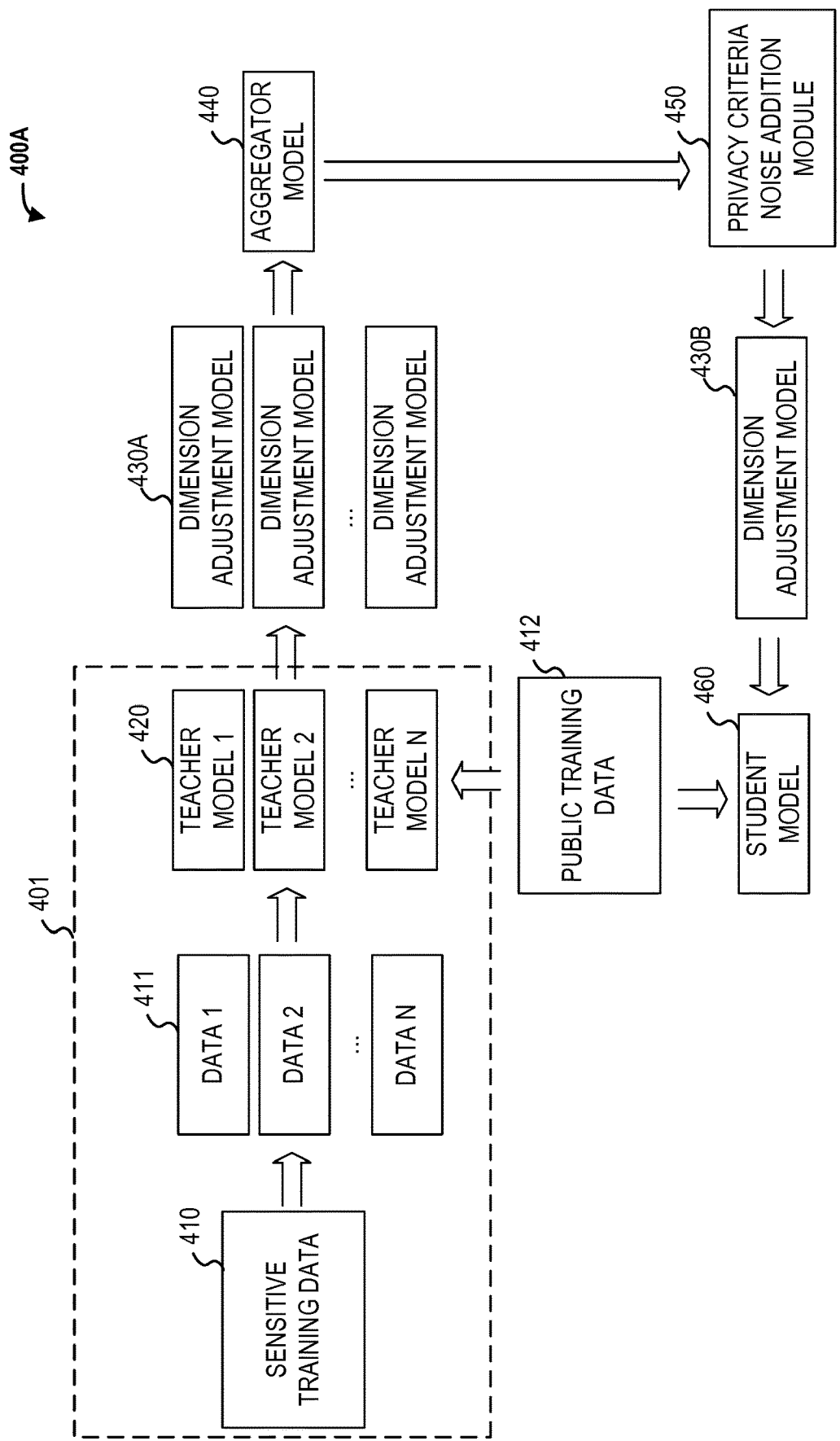
FIGS. 4A and 4B illustrate an exemplary data flow for training and use of a machine learning model(s) to provide privacy, according to some examples of the disclosure.

FIG. 4A illustrates an exemplary data flow 400A for training and use of one or more private and public machine learning models to generate a radiotherapy treatment plan, according to some examples of the disclosure. The data flow 400A includes teacher ML model training portion 401, dimension adjustment ML models 430A and 430B, aggregator ML model 440, privacy criteria noise addition module 450, student ML model 460, and public training data 412. The ML models discussed in connection with FIGS. 4A and 4B may be trained and applied in a similar manner as discussed above in connection with FIG. 3.

Initially, the teacher ML model training portion 401 operates on a set of private and sensitive training data 410 to train a plurality of teacher ML models 420. Each of the plurality of teacher ML models 420 may be identical in implementation and leverage a common set of ML parameters 312. In some implementations, the sensitive training data 410 is provided by one or more hospitals and/or patients. The sensitive training data 410 may include one or more pairs of labels or segmentations of radiotherapy medical images (e.g., CT, MR and/or sCT images); pairs of a 3D model and one or more corresponding radiotherapy medical images; pairs of a dose distribution and one or more radiotherapy images; pairs of a sCT image and a CT image; pairs of control points and one or more radiotherapy images and/or MR scan distance maps; and pairs of individual radiotherapy plan parameter estimates and aggregated results of the plurality of training individual radiotherapy plan parameter estimates. The pairs included among the sensitive training data 410 may depend on the type of teacher ML model 420 that is used. For example, when the teacher ML model 420 and its complement student ML model 460 are configured to generate labels or segment for CT images, the pairs of sensitive training data 410 may include pairs of CT images and corresponding labels. As another example, when the teacher ML model 420 and its complement student ML model 460 are configured to generate sCT images for a CT image, the pairs of sensitive training data 410 may include pairs of sCT images and corresponding CT images.

The sensitive training data 410 may be divided into disjoint datasets 411. Each dataset 411 is provided to a respective instance of the teacher ML models 420. In one example, the datasets 411 in one set may include a set of the sensitive training data 410 from one hospital and/or one collection of patients and the datasets 411 in another set may include a set of the sensitive training data 410 from another hospital and/or another collection of patients. The sensitive training data 410 may be inaccessible by unauthorized parties outside of the portion 401. Namely, the sensitive training data 410 may be stored in one or more secure databases external to the public training data 412 and/or student model 460.

As an example, when the teacher ML models 420 are configured to generate labels or segments for CT images, the teacher ML models 420 operate on various sets of the sensitive training data 410 to be trained to estimate labels or segment a CT image given the CT image. For example, the teacher ML models 420 may receive a respective training CT image and generate respective labels or segments for the training CT image. The generated respective labels or segments are compared with ground truth labels or segments in the paired training data. Based on a deviation between the generated respective labels or segments and ground truth labels or segments in the paired training data and a loss function associated with the teacher ML models, the teacher ML model parameters are updated until a threshold number of iterations of pairs of training data is processed and/or until a deviation reaches a threshold amount.

After being trained, the teacher models 420 process public training data 412 to generate radiotherapy treatment plan parameters for the public training data 412. For example, the public training data 412 may include un-labeled un-segmented CT images. The teacher models 420 process the public training data 412 to generate labels or segment the CT images in the public training data 412. The results are provided to a trained dimension adjustment ML model 430A. The trained dimension adjustment ML model 430A may include a variational autoencoder, an autoencoder, principal component analysis, or homomorphic compression trained based on public segmentation maps. The trained dimension adjustment ML model 430A may reduce a dimension of the labeled CT images generated by the teacher ML models 420.

After reducing a dimension of the labeled CT images generated by the teacher ML models 420, the output of the trained dimension adjustment ML model 430A is processed by an aggregator ML model 440. In an embodiment, the aggregator ML model 440 computes a mean, a trimmed mean, a median, or a generalized f-mean of the individual reduced dimension labeled CT images generated by the teacher ML models 420. In other embodiments, the aggregator ML model 440 processes the received individual reduced dimension labeled CT images and estimates an aggregation of the individual reduced dimension labeled CT images.

An output of the aggregator ML model 440 is provided to the privacy criteria noise addition module 450. Privacy criteria noise addition module 450 adds noise to the aggregated information provided by the aggregator ML model 440 according to a selected privacy criteria level. The privacy criteria can include differential privacy, Rényi differential privacy, concentrated differential privacy, mutual information, conditional entropy, Fisher information, generative adversarial privacy, or k-anonymity. The privacy criteria noise addition module 450 adds noise to the aggregated information by adding samples from a Gaussian, Beta, Dirichlet, or Laplace distribution based on the privacy criteria.

Differential privacy offers a rigorous guarantee for database access mechanisms. It is based on the notion of dataset adjacency (also referred to as neighborhood): two datasets d, d' are defined to be adjacent if they differ in the presence of a single dataset record. Differential privacy then requires that the outputs of a mechanism be indistinguishable for adjacent inputs. A randomized mechanism M: D→R satisfies ($\epsilon$, $\delta$)–differential privacy if for any two adjacent inputs d, d'∈ D and for any S⊆R, Pr[M(d)∈ S]≤$e^\epsilon$Pr[M(d')∈ S]+$\delta$.

According to some embodiments, a record is an image-segmentation pair and M is a randomized training algorithm. That is, M(d) is a random variable that represents the model parameters of the ML model, M, are trained on dataset d. In an implementation, the randomness comes from the training algorithm, not from the data. Differential privacy is agnostic towards the data distribution, thus d is treated as a constant.

The output of the privacy criteria noise addition module 450 is provided to the dimension adjustment model 430B. Dimension adjustment model 430B may perform the reverse operation of dimension adjustment model 430A. Namely, dimension adjustment model 430B may increase or restore the dimension of the now noise aggregated information that is provided by the privacy criteria noise addition module 450. The output of the dimension adjustment model 430B is provided to the student ML model 460 to train the student ML model 460. Namely, the student ML model 460 can now be trained based on the public training data 412 using the privatized noisy estimates of the radiotherapy treatment plan parameters provided by the trained teacher models 420. The privacy parameters $\epsilon$ and $\delta$ also straight-forwardly translate to lower bounds on the false-positive and false-negative rate of any discriminator that tries to distinguish between d and d'. This may also be helpful in deciding which parameter values can be considered strong enough.

A randomized mechanism privacy criteria M: D→R satisfies ($\epsilon$, $\delta$)–differential privacy if and only if the following conditions are satisfied for any two adjacent inputs d, d'∈ D and any rejection region S⊆R:

$$P_{FP}(d,d',M,S)+e^\epsilon P_{FN}(d,d',M,S) \geq 1-\delta$$

$$e^\epsilon P_{FP}(d,d',M,S)+P_{FN}(d,d',M,S) \geq 1-\delta$$

where $P_{FP}$ and $P_{FN}$ are, respectively, the false-positive rate and false-negative rate for the classifier that outputs d if M∈ S and d' otherwise. There are a few basic mechanisms that add differential privacy to existing non-private functions. They are based the notion of the function's sensitivity.

The $l_p$-sensitivity $S_p(f)$ of a function f: D→$R^n$ is defined as:

$$S_p(f) = \max_{d,d'}\|f(d) - f(d')\|_p$$

where the maximum is taken over adjacent d, d'∈ D. The standard mechanisms then add noise to a function, calibrated to the sensitivity and privacy parameters. For Laplace mechanism privacy criteria, let f: D→$R^n$ be a function and Lap(b) be the Laplace distribution with scale b. If $\alpha_1, \ldots,$ $$\alpha_n \underset{iid}{\sim} Lap\left(\frac{S_1(f)}{\epsilon}\right)$$

and $\alpha=(\alpha_1, \ldots, \alpha_n)^T$ then the mechanism M(d)=f (d)+$\alpha$ is ($\epsilon$, 0) is differentially private. For Gaussian mechanism privacy criteria, Let f: D→$R^n$ be a function and N ($\mu$, $\sigma^2$) be the Normal distribution with mean g and variance $\sigma^2$. Let $$\sigma = \frac{cS_2(f)}{\epsilon}$$

with $c^2>2$ ln(1.25/$\delta$). If $\alpha_1, \ldots,$ $$\alpha_n \underset{iid}{\sim} N(0, \sigma^2)$$

and $\alpha=(\alpha_1, \ldots, \alpha_n)^T$ then the mechanism M(d)=f (d)+$\alpha$ is ($\epsilon$, $\delta$) is differentially private. Rényi Differential Privacy is a generalization of differential privacy in the sense that every Rényi Differential Privacy mechanism satisfies differential privacy but not the other way around. Due to its stricter requirements, it allows for a sharper analysis of cumulative privacy loss and defines indistinguishability in terms of the more general Rényi divergence.

For Rényi divergence privacy criteria, let X~p and Y~q be random variables. Their Rényi divergence of order a is defined as $$D_\alpha(X \| Y) = \frac{1}{\alpha - 1}\log\mathbb{E}\left[\left(\frac{p(Y)}{q(Y)}\right)^\alpha\right]$$

for any $\alpha>1$. Rényi Differential Privacy requires the Rényi divergence of the outputs of a mechanism to be small when run on adjacent inputs. For Rényi Differential Privacy, a randomized mechanism M: D 1→R satisfies ($\alpha$, $\epsilon$) Rényi Differential Privacy if for any two adjacent inputs d, d'∈ D $D_\alpha$(M(d)$\|$M(d'))≤$\epsilon$.

Another privacy criteria is k-anonymity, which is a property of databases. For a set of quasi identifiers recorded in the database—such as zip code or date of birth—k-anonymity demands that any combination of values of the quasi identifiers that is present in the database occurs at least k times.

Another privacy criterion is conditional entropy, for which X given Y is defined as:

$$H(X \mid Y) = -\sum_y \sum_x p(y, x)\log_2 p(x \mid y)$$

and intuitively represents the additional number of bits needed to describe X after having observed Y. In a machine learning context, Y could refer to the model parameters and X to the training data. A high conditional entropy would then limit the ability of an adversary to reconstruct the training set from the published model parameters. Conditional entropy implies a lower bound on the expected estimation error.

Another privacy criterion is mutual information, in which the mutual information between X and Y is defined as:

$$I(X, Y) = -\sum_y \sum_x p(y, x)\log_2 \frac{p(x, y)}{p(x)p(y)}$$

and intuitively represents the amount of information shared between X and Y. Alternatively, one can describe mutual information as the amount of information gained about X by observing Y. While conditional entropy limits certainty of the reconstruction of the training data, mutual information instead limits the reduction of uncertainty. Conditional entropy and mutual information are directly related through entropy, which describes how uncertain an adversary is about X before observing Y. Mutual information is precisely the difference between entropy and conditional entropy.

Another privacy criterion is generative adversarial privacy, which is a privacy definition inspired by generative adversarial networks. In a constrained minimax game, an adversarial model is trained alongside a privacy-preserving generative model. The goal of the former is to predict private attributes from public ones while the latter minimizes the adversary's prediction performance. Thereby, the data holder implicitly learns a privatization scheme from the data. This scheme is data-dependent but does not require detailed knowledge of the data distributions, thus trying to combine the best of both worlds.

Figure 4B:
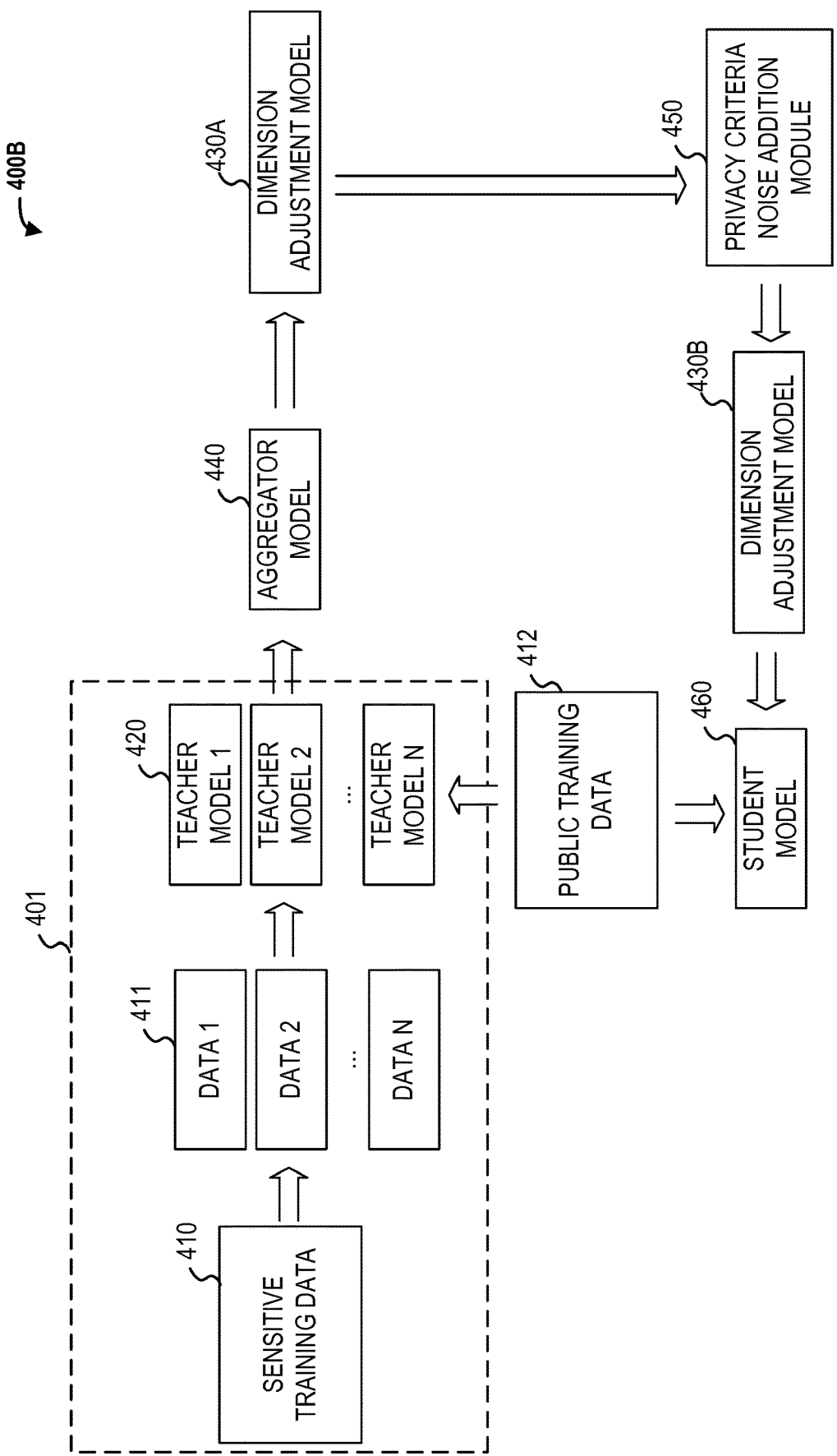

FIG. 4B illustrates an exemplary data flow 400B for training and use of one or more private and public machine learning models to generate a radiotherapy treatment plan, according to some examples of the disclosure. Data flow 400B is identical in operation to data flow 400A except that the aggregator ML model 440 is applied directly to the outputs of the trained teacher ML models 420 rather than the reduced dimension outputs. In data flow 400B, after the outputs of the trained teacher ML models 420 are aggregated in a similar manner as in data flow 400A, the aggregated information is provided to the dimension adjustment ML model 430A to reduce the dimension of the aggregated information. The reduced dimension aggregated information is provided by the dimension adjustment model 430A to the privacy criteria noise addition module 450. And, as in data flow 400A, the output of the privacy criteria noise addition module 450 is provided to the student model 460 after passing through the dimension adjustment ML model 430B to restore or increase the dimension of the information.

Figure 5:
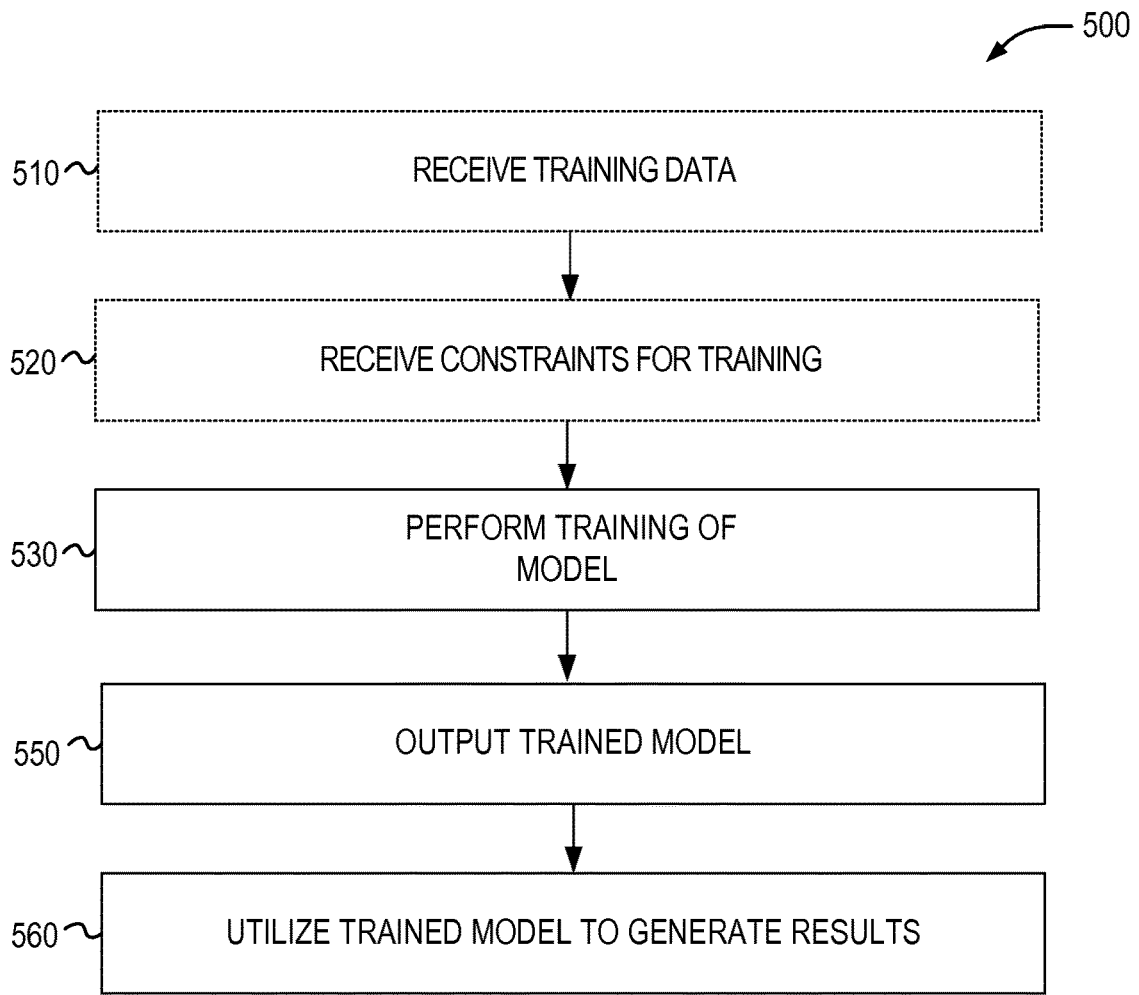
FIGS. 5-7 illustrate flowcharts of exemplary operations for training and using a machine learning model in a way that maintains data privacy, according to some examples of the disclosure.

FIG. 5 is a flowchart illustrating example operations of the treatment processing logic 120 in performing process 500, according to example embodiments. The process 500 may be embodied in computer-readable instructions for execution by one or more processors such that the operations of the process 500 may be performed in part or in whole by the functional components of the treatment processing logic 120; accordingly, the process 500 is described below by way of example with reference thereto. However, in other embodiments, at least some of the operations of the process 500 may be deployed on various other hardware configurations. The process 500 is therefore not intended to be limited to the treatment processing logic 120 and can be implemented in whole, or in part, by any other component. Some or all of the operations of process 500 can be in parallel, out of order, or entirely omitted.

At operation 510, treatment processing logic 120 receives training data. For example, treatment processing logic 120 receives training data 320, which may include paired training data sets 322 (e.g., input-output training pairs).

At operation 520, treatment processing logic 120 receives constraints for training the model. For example, treatment processing logic 120 receives constraints 326.

At operation 530, treatment processing logic 120 performs training of the model.

At operation 550, treatment processing logic 120 outputs the trained model. For example, treatment processing logic 120 outputs the trained model 360 to operate on a new set of input data 370.

At operation 560, treatment processing logic 120 utilizes the trained model 360 to generate a radiotherapy plan. For example, treatment processing logic 120 utilizes the trained model 360 to operate on a new set of input data 370.

Figure 6:
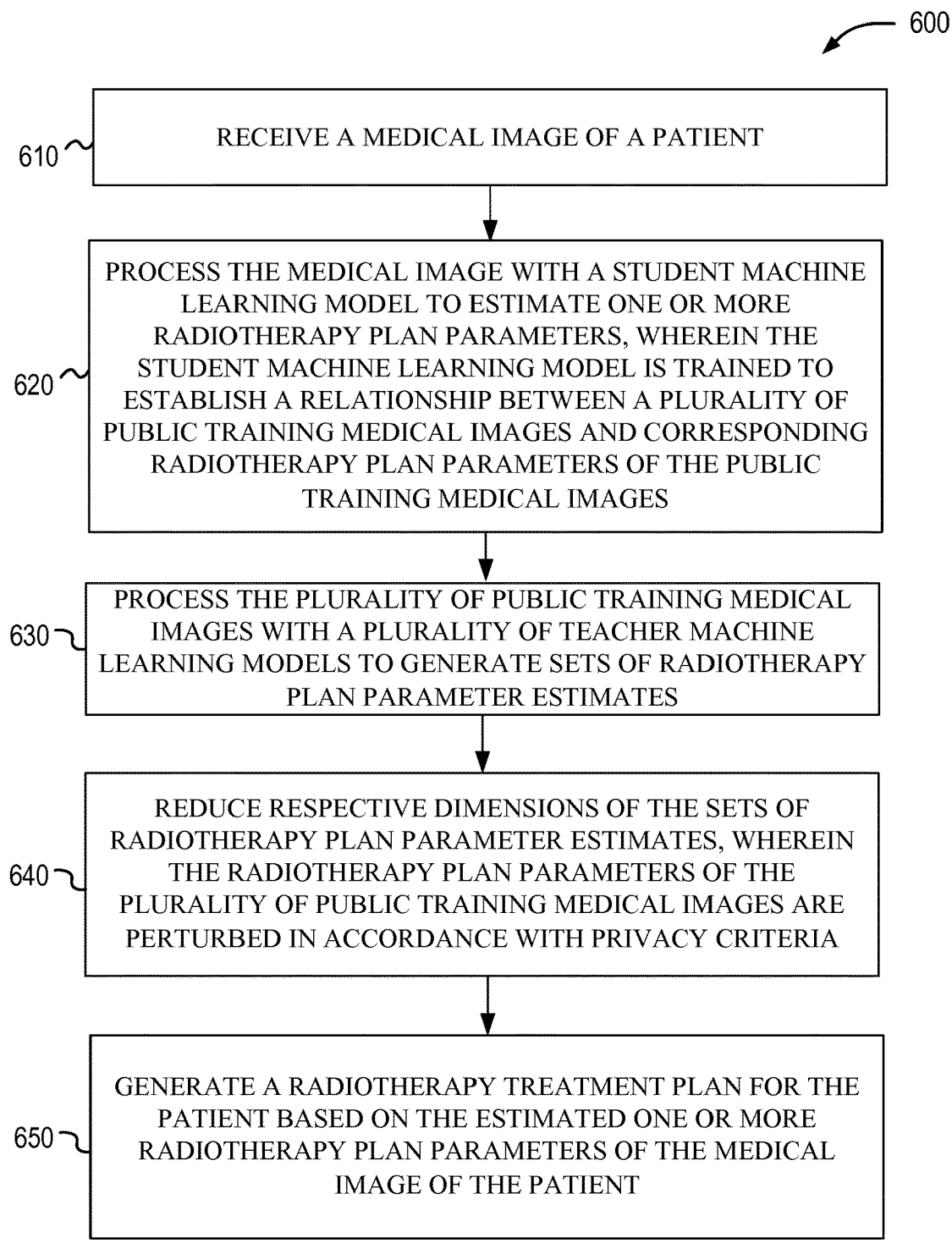

FIG. 6 is a flowchart illustrating example operations of the treatment processing logic 120 in performing a process 600, according to example embodiments. The process 600 may be embodied in computer-readable instructions for execution by one or more processors such that the operations of the process 600 may be performed in part or in whole by the functional components of the treatment processing logic 120; accordingly, the process 600 is described below by way of example with reference thereto. However, in other embodiments, at least some of the operations of the process 600 may be deployed on various other hardware configurations. The process 600 is therefore not intended to be limited to the treatment processing logic 120 and can be implemented in whole, or in part, by any other component. Some or all of the operations of process 600 can be in parallel, out of order, or entirely omitted.

At operation 610, treatment processing logic 120 receives a medical image of a patient.

At operation 620, treatment processing logic 120 processes the medical image with a student machine learning model to estimate one or more radiotherapy plan parameters, wherein the student machine learning model is trained to establish a relationship between a plurality of public training medical images and corresponding radiotherapy plan parameters of the public training medical images.

At operation 630, treatment processing logic 120 processes the plurality of public training medical images with a plurality of teacher machine learning models to generate sets of radiotherapy plan parameter estimates.

At operation 640, treatment processing logic 120 reduces respective dimensions of the sets of radiotherapy plan parameter estimates, wherein the radiotherapy plan parameters of the plurality of public training medical images are perturbed in accordance with privacy criteria.

At operation 650, treatment processing logic 120 generates a radiotherapy treatment plan for the patient based on the estimated one or more radiotherapy plan parameters of the medical image of the patient.

Figure 7:
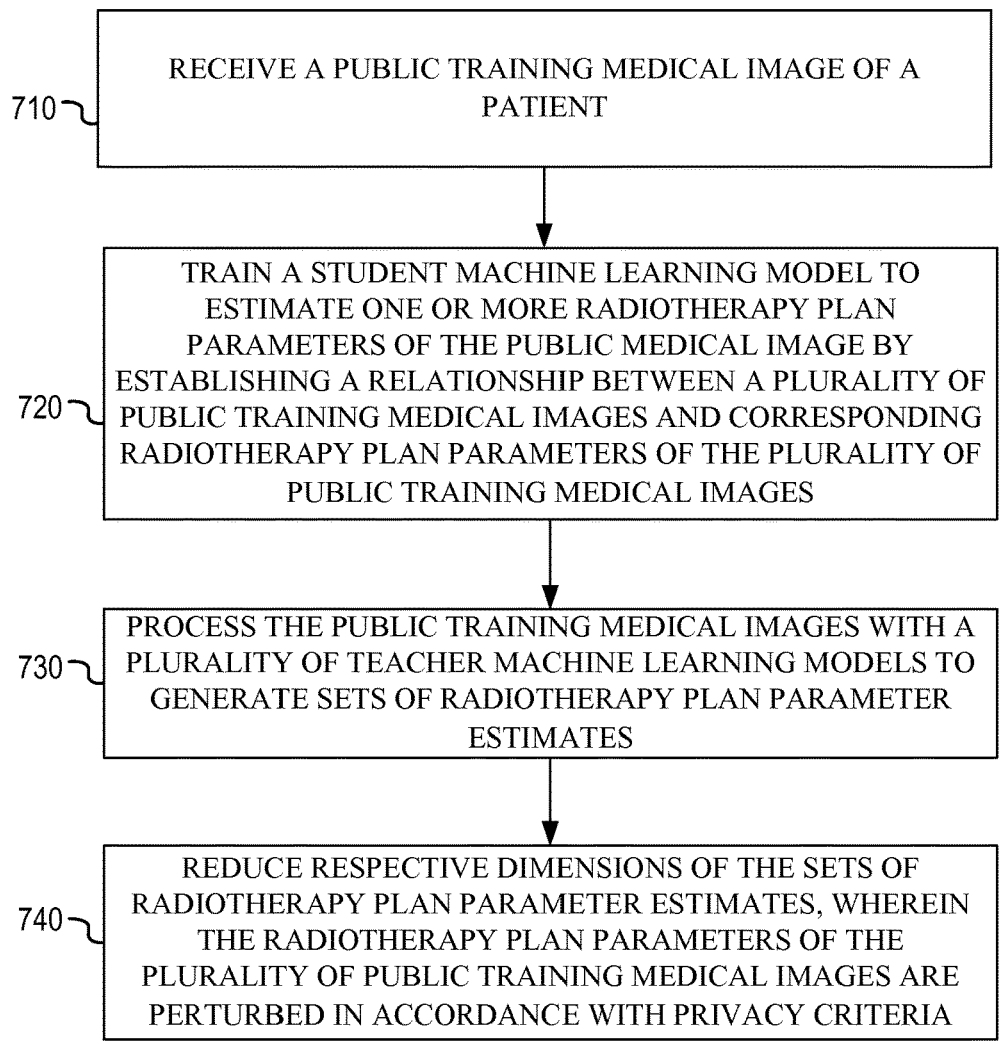

FIG. 7 is a flowchart illustrating example operations of the treatment processing logic 120 in performing process 700, according to example embodiments. The process 700 may be embodied in computer-readable instructions for execution by one or more processors such that the operations of the process 700 may be performed in part or in whole by the functional components of the treatment processing logic 120; accordingly, the process 700 is described below by way of example with reference thereto. However, in other embodiments, at least some of the operations of the process 700 may be deployed on various other hardware configurations. The process 700 is therefore not intended to be limited to the treatment processing logic 120 and can be implemented in whole, or in part, by any other component. Some or all of the operations of process 700 can be in parallel, out of order, or entirely omitted.

At operation 710, treatment processing logic 120 receives a public training medical image of a patient.

At operation 720, treatment processing logic 120 trains a student machine learning model to estimate one or more radiotherapy plan parameters of the public medical image by establishing a relationship between a plurality of public training medical images and corresponding radiotherapy plan parameters of the plurality of public training medical images.

At operation 730, treatment processing logic 120 processes the public training medical images with a plurality of teacher machine learning models to generate sets of radiotherapy plan parameter estimates.

At operation 740, treatment processing logic 120 reduces respective dimensions of the sets of radiotherapy plan parameter estimates, wherein the radiotherapy plan parameters of the plurality of public training medical images are perturbed in accordance with privacy criteria.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 202, perform or implement the training or prediction operations from FIG. 3, operate the trained model 360, perform or implement the operations of the flowcharts for processes 500-700, or perform any one or more of the other methodologies discussed herein (e.g., as part of treatment processing logic 120). In various embodiments, such electronic computing systems or devices operate as standalone devices or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of claims of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims (aspects), the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that objects after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of claims of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and example parameters, functions, and implementations described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method for performing privacy based radiotherapy treatment planning, the method comprising:
    receiving, by processor circuitry, a medical image of a patient;
    processing, by the processor circuitry, the medical image with a student machine learning model to estimate one or more radiotherapy plan parameters, wherein the student machine learning model is trained to establish a relationship between a plurality of public training medical images and corresponding radiotherapy plan parameters of the public training medical images, wherein the radiotherapy plan parameters of the plurality of public training medical images are generated by aggregating a plurality of radiotherapy plan parameter estimates which have been produced by:
        processing the plurality of public training medical images with a plurality of teacher machine learning models to generate sets of radiotherapy plan parameter estimates; and
        reducing respective dimensions of the sets of radiotherapy plan parameter estimates or the plurality of public training medical images, wherein the radiotherapy plan parameters of the plurality of public training medical images are perturbed in accordance with a privacy criteria; and
    generating, by the processor circuitry, a radiotherapy treatment plan for the patient based on the estimated one or more radiotherapy plan parameters of the medical image of the patient.

2. The method of claim 1, wherein the student machine learning model and the plurality of teacher machine learning models are implemented by respective neural networks or deep learning networks.

3. The method of claim 1 further comprising training the teacher machine learning models based on private medical information comprising private medical images and private radiotherapy plan parameters of the private medical images, wherein the student machine learning model is trained on data that excludes the private medical information.

4. The method of claim 3, wherein training the teacher machine learning models comprises:
    generating disjoint datasets from the private medical information; and
    training the teacher machine learning models based on respective ones of the disjoint datasets.

5. The method of claim 1 further comprising:
    generating a first of the plurality of radiotherapy plan parameter estimates by processing the plurality of public training medical images with a first of the plurality of trained teacher machine learning models;
    generating a second of the plurality of radiotherapy plan parameter estimates by processing the plurality of public training medical images with a second of the plurality of trained teacher machine learning models;
    reducing a dimension of each of the first and second of the plurality of radiotherapy plan parameter estimates to produce reduced dimension first and second radiotherapy plan parameter estimates; and
    aggregating the reduced dimension first and second radiotherapy plan parameter estimates.

6. The method of claim 5, wherein the first of the plurality of radiotherapy plan parameter estimates includes a first number of entries, and wherein the reduced dimension first radiotherapy plan parameter estimate includes a second number of entries that is smaller than the first number of entries.

7. The method of claim 1, wherein aggregating the reduced dimension first and second radiotherapy plan parameter estimates comprises computing a mean, a trimmed mean, a median, or a generalized f-mean of the reduced dimension first and second radiotherapy plan parameter estimates.

8. The method of claim 1, wherein aggregating the reduced dimension first and second radiotherapy plan parameter estimates comprises estimating an aggregation of the reduced dimension first and second radiotherapy plan parameter estimates by processing the reduced dimension first and second radiotherapy plan parameter estimates with an aggregation machine learning model, wherein the aggregation machine learning model is trained to establish a relationship between a plurality of training individual radiotherapy plan parameter estimates and aggregated results of the plurality of training individual radiotherapy plan parameter estimates and to minimize an amount of perturbation needed to satisfy the privacy criteria.

9. The method of claim 1 further comprising perturbing at least one of the reduced dimension first and second radiotherapy plan parameter estimates or the aggregated reduced dimension first and second radiotherapy plan parameter estimates by adding noise based on a selected privacy level to the at least one of the reduced dimension first and second radiotherapy plan parameter estimates or the aggregated reduced dimension first and second radiotherapy plan parameter estimates.

10. The method of claim 9, wherein adding noise comprises adding samples from a Gaussian, Beta, Dirichlet, or Laplace distribution to at least one of the reduced dimension first and second radiotherapy plan parameter estimates or the aggregated reduced dimension first and second radiotherapy plan parameter estimates.

11. The method of claim 1 further comprising increasing a dimension of the perturbed aggregated reduced dimension first and second radiotherapy plan parameter estimates to output the plurality of radiotherapy plan parameters.

12. The method of claim 11, wherein increasing the dimension comprises processing the perturbed aggregated reduced dimension first and second radiotherapy plan parameter estimates with a variational autoencoder, autoencoder, principal component analysis, or homomorphic compression.

13. The method of claim 1, wherein reducing the dimension of each of the first and second of the plurality of radiotherapy plan parameter estimates comprises processing each of the first and second of the plurality of radiotherapy plan parameter estimates with a variational autoencoder, autoencoder, principal component analysis, or homomorphic compression.

14. The method of claim 13, wherein the variational autoencoder, the autoencoder, or the principal component analysis is trained based on a public set of segmentation maps.

15. The method of claim 1, wherein the privacy criteria comprise at least one of differential privacy, Rényi differential privacy, concentrated differential privacy, mutual information, conditional entropy, Fisher information, generative adversarial privacy, or k-anonymity.

16. The method of claim 1, wherein the medical image comprises a magnetic resonance (MR) image or computed tomography (CT), and wherein the one or more radiotherapy plan parameters include at least one of labels for the medical image, a three-dimensional volume corresponding to the medical image, a dose distribution, a synthetic CT image, the medical image, a processed version of the medical image, or radiotherapy device parameters.

17. A non-transitory computer-readable medium comprising non-transitory computer-readable instructions, the computer-readable instructions comprising instructions for performing operations comprising:
receiving a medical image of a patient;
processing the medical image with a student machine learning model to estimate one or more radiotherapy plan parameters, wherein the student machine learning model is trained to establish a relationship between a plurality of public training medical images and corresponding radiotherapy plan parameters of the public training medical images, wherein the radiotherapy plan parameters of the plurality of public training medical images are generated by aggregating a plurality of radiotherapy plan parameter estimates which have been produced by:
processing the plurality of public training medical images with a plurality of teacher machine learning models to generate sets of radiotherapy plan parameter estimates; and
reducing respective dimensions of the sets of radiotherapy plan parameter estimates or the plurality of public training medical images, wherein the radiotherapy plan parameters of the plurality of public training medical images are perturbed in accordance with privacy criteria; and
generating a radiotherapy treatment plan for the patient based on the estimated one or more radiotherapy plan parameters of the medical image of the patient.

18. The non-transitory computer readable medium of claim 17, wherein the student machine learning model and the plurality of teacher machine learning models are implemented by respective neural networks or deep learning networks.

19. The non-transitory computer readable medium of claim 17, wherein the operations further comprise training the teacher machine learning models based on private medical information comprising private medical images and private radiotherapy plan parameters of the private medical images, wherein the student machine learning model is trained on data that excludes the private medical information.

20. A system comprising:
a memory for storing instructions; and
one or more processors for executing the instructions stored in the memory for performing operations comprising:
receiving a medical image of a patient;
processing the medical image with a student machine learning model to estimate one or more radiotherapy plan parameters, wherein the student machine learning model is trained to establish a relationship between a plurality of public training medical images and corresponding radiotherapy plan parameters of the public training medical images, wherein the radiotherapy plan parameters of the plurality of public training medical images are generated by aggregating a plurality of radiotherapy plan parameter estimates which have been produced by:
processing the plurality of public training medical images with a plurality, of teacher machine learning models to generate sets of radiotherapy plan parameter estimates; and
reducing respective dimensions of the sets of radiotherapy plan parameter estimates or the plurality of public training medical images, wherein the radiotherapy plan parameters of the plurality of public training medical images are perturbed in accordance with privacy criteria; and
generating a radiotherapy treatment plan for the patient based on the estimated one or more radiotherapy plan parameters of the medical image of the patient.

* * * * *

UNITED STATES PATENT AND TRADEMARK OFFICE
CERTIFICATE OF CORRECTION

PATENT NO. : 11,975,218 B2
APPLICATION NO. : 17/595488
DATED : May 7, 2024
INVENTOR(S) : Fay et al.

Page 1 of 1

It is certified that error appears in the above-identified patent and that said Letters Patent is hereby corrected as shown below:

In the Claims

In Column 32, Line 51, in Claim 20, delete "plurality," and insert --plurality-- therefor Signed and Sealed this
Eighth Day of July, 2025

Coke Morgan Stewart
*Acting Director of the United States Patent and Trademark Office*